United States Patent
Chevallet et al.

(10) Patent No.: US 7,291,269 B2
(45) Date of Patent: Nov. 6, 2007

(54) APPARATUS AND PROCESS FOR EXTRACORPOREAL TREATMENT OF BLOOD WITH SELECTIVE EXTRACTION OF SOLUTES

(75) Inventors: Jacques Chevallet, Serezin du Rhone (FR); Guy Mercier, Bron (FR); Hiram Rada, Lyons (FR); Mehran Monchi, Dammarie les Lys (FR)

(73) Assignee: Gambro Lundia AB, Lund (SE)

( * ) Notice: Subject to any disclaimer, the term of this patent is extended or adjusted under 35 U.S.C. 154(b) by 313 days.

(21) Appl. No.: 10/801,830

(22) Filed: Mar. 17, 2004

(65) Prior Publication Data
US 2004/0182787 A1 Sep. 23, 2004

Related U.S. Application Data

(60) Provisional application No. 60/456,520, filed on Mar. 24, 2003.

(30) Foreign Application Priority Data

Mar. 17, 2003 (FR) .................................. 03 03257

(51) Int. Cl.
*B01D 61/00* (2006.01)
*B01D 61/18* (2006.01)
*B01D 61/22* (2006.01)
*B01D 61/24* (2006.01)
*B01D 61/28* (2006.01)
*B01D 61/32* (2006.01)
*A61M 1/34* (2006.01)
*A61M 1/16* (2006.01)

(52) U.S. Cl. .......................... 210/650; 210/85; 210/86; 210/87; 210/97; 210/104; 210/134; 210/143; 210/195.1; 210/195.2; 210/252; 210/257.1; 210/258; 210/321.6; 210/321.65; 210/645; 210/646; 604/4.01; 604/5.01; 604/5.04; 604/6.01; 604/6.04; 604/6.09; 604/6.11

(58) Field of Classification Search .................. 210/85, 210/86, 87, 97, 104, 134, 143, 195.1, 195.2, 210/252, 258, 257.1, 321.6, 321.65, 645, 210/646, 650, 739; 604/4.01, 5.01, 5.04, 604/6.01, 6.04, 6.09, 6.11
See application file for complete search history.

(56) References Cited

U.S. PATENT DOCUMENTS 3,619,423 A 11/1971 Galletti et al. ................. 210/22

(Continued)

FOREIGN PATENT DOCUMENTS

DE 4102693 8/1992

(Continued)

OTHER PUBLICATIONS

P. Aebischer, et al., "The Bioartificial Kidney: Progress towards an Ultrafiltration Device with Renal Epithelial Cells Processing," *Life Support Systems* (1987), 5, pp. 159-168.

(Continued)

*Primary Examiner*—John Kim
(74) *Attorney, Agent, or Firm*—Finnegan, Henderson, Farabow, Garrett & Dunner, L.L.P.

(57) ABSTRACT

A device and method for an extracorporeal blood treatment is described. The device comprising at least one exchanger equipped with at least one first inlet for the blood to be treated, a first fluid outlet and a second fluid outlet, an input line for blood to be treated connected to the first inlet of the exchanger, a blood output line (or venous line) connected to the first outlet of the exchanger, at least one treatment unit comprising at least one first fluid inlet and at least one first fluid outlet, the second outlet of the exchanger being in fluid communication with the first inlet of the treatment unit, where the first outlet from the treatment unit is in fluid communication with the input line and the second outlet of the treatment unit is in fluid communication with a first waste liquid discharge line.

38 Claims, 9 Drawing Sheets

U.S. PATENT DOCUMENTS

| | | | |
|---|---|---|---|
| 4,243,532 A | | 1/1981 | Tsuda et al. ................ 210/196 |
| 4,960,408 A | * | 10/1990 | Klainer et al. ............. 604/6.08 |
| 5,108,612 A | | 4/1992 | Flaig et al. ................. 210/651 |
| 5,211,849 A | * | 5/1993 | Kitaevich et al. .......... 604/5.04 |
| 5,366,630 A | * | 11/1994 | Chevallet .................... 210/645 |
| 5,536,412 A | * | 7/1996 | Ash ........................... 210/645 |
| 5,679,245 A | * | 10/1997 | Manica ....................... 210/134 |
| 6,193,681 B1 | | 2/2001 | Davidner et al. .......... 604/6.08 |
| 6,406,631 B1 | | 6/2002 | Collins et al. ............. 210/646 |
| 6,423,231 B1 | | 7/2002 | Collins et al. ............. 210/646 |
| 6,561,997 B1 | * | 5/2003 | Weitzel et al. ............. 604/6.09 |
| 6,582,385 B2 | * | 6/2003 | Burbank et al. ........... 604/5.04 |
| 6,730,233 B2 | * | 5/2004 | Pedrazzi ..................... 210/739 |
| 6,787,040 B2 | * | 9/2004 | Radunsky et al. .......... 210/651 |
| 2005/0043666 A1 | * | 2/2005 | Pan ............................ 604/6.08 |

FOREIGN PATENT DOCUMENTS

| | | |
|---|---|---|
| DE | 19854338 | 6/2000 |
| EP | 0 832 656 A1 | 4/1998 |
| WO | WO 95/04560 | 2/1995 |
| WO | WO 96/28198 | 9/1996 |
| WO | WO 02/36247 A1 | 5/2002 |
| WO | WO 02/49745 A1 | 6/2002 |

OTHER PUBLICATIONS

T. Eisenhauer, et al., "Selective Continuous Elimination of Low Density Lipoproteins (LDL) by Heparin Precipitation: First Clinical Application," vol. XXXII *Trans Am Soc Artif Intern Organs* 1986, pp. 104-107.

Thor M. Svartaas, et al., "Selection of Filters and Evaluation In Vitro of the Selective Dual Filtration Artificial Kidney, SEDUFARK," *Artificial Organs*, vol. 6, No. 2, pp. 136-144 (1982).

U.R. Shettigar, "Innovative Extracorporeal Membrane Systems," *Journal of Membrane Science*, 44 (1989) pp. 89-114.

Tze Kin Ip and Patrick Aebischer, "Renal Epithelia-Cell-Controlled Solute Transport Across Permeable Membranes as the Foundation for a Bioartificial Kidney," *Artif Organs*, vol. 13, No. 1, 1989, pp. 58-65.

Dr. J.C. Kingswood and Dr. F.D. Thompson, *Proposal For A Double Membrane Artificial Kidney* undated.

A. Murisasco, et al., "The Wearable Kidney," *Trans Amer Soc Artif Intern Organs* 1986; 32;567-71.

International Search Report for International Application No. PCT/IB2004/000896.

International Preliminary Report on Patentability for International Application No. PCT/IB2004/000896.

* cited by examiner

Fig. 1 — Prior art
Principle of reinjection in post-dilution

Fig. 2 — Prior art
Principle of reinjection in post-dilution

Fig 3. — Prior art

Fig. 4 — Principle of the invention

Fig. 5

Fig. 6 – Exchanger in dialysis mode

Fig. 7 – Treatment unit in dialysis mode

Fig. 8 – Auxiliary exchanger in dialysis mode

Plasmapheresis

APPARATUS AND PROCESS FOR EXTRACORPOREAL TREATMENT OF BLOOD WITH SELECTIVE EXTRACTION OF SOLUTES

CROSS REFERENCE TO RELATED APPLICATIONS

This application claims priority of French patent application No. 03 03257, filed on Mar. 17, 2003 and the benefit of U.S. Provisional Application No. 60/456,520, filed on Mar. 24, 2003, the contents of which are incorporated herein by reference.

BACKGROUND OF THE INVENTION

1. Filed of the Invention

The object of the present invention is a device and a method for the treatment of blood with selective extraction of solutes.

The object of this patent application is the filtration of blood to selectively separate and extract dissolved substances of chosen molecular size by means of extracorporeal systems designed for the separation of substances.

2. Description of Related Art

Such systems are used for the treatment of blood containing solutes with different molecular weights. Such substances are, for example, urea, of molecular weight 60 daltons, phosphate (96-97 daltons), creatinine (113 daltons), vitamin $B_{12}$ (1 355 daltons), inulin (5 200 daltons), beta 2-microglobulin (12 000 daltons), and albumin (58 000 daltons).

Are hereafter termed 'small-sized molecules' molecules of molecular weight less than about 2 000 daltons, 'medium-sized molecules' molecules of molecular weight between 2 000 and 50 000 daltons, and 'large-sized molecules' molecules of molecular weight greater than 50 000 daltons (for example, proteins).

Such systems are often systems with extracorporeal membranes for the separation of solutes of molecular weight lower than that of albumin, applied to the treatment of renal insufficiency.

Improvements have always been sought in particular to ameliorate clearance, reduce treatment time and to make such systems simpler and less costly. The clearance of a solute is the amount of that solute in a given volume of treated blood.

In the field of dialysis, the first membranes used were highly permeable to small solutes of molecular weight up to 200 daltons. The clearance of small solutes depends on the permeability and diffusion capacity of the membrane used.

The lack of permeability of the first membranes for certain medium-sized solutes in the vitamin $B_{12}$ range (1 355 daltons) was blamed for the occurrence of multiple uraemic neuropathies.

To improve the clearance of medium-sized molecules, a first response was to add to the diffusion flow through the membrane a convection flow using high flow membranes with a molecular size cut-off value of 40 000 daltons. The cut-off value of a membrane is defined as the molecular size for which no more than 10% of the solute travels through the membrane.

However, problems met in embodying this response include difficulty in controlling the ultrafiltration rate obtained by the convection flow, and the high loss of useful plasma constituents such as hormones, vitamins and amino acids.

A second response for the improvement of the clearance of medium-sized molecules was haemo-filtration, a purely convective method for the elimination of solutes by the membrane. However, this method extracts a large amount of liquid, therefore requiring a compensatory pre- and (or) post-dilution with sterile liquid, and a membrane that is highly permeable to solutes of molecular weight up to 40 000 daltons. However, in a purely convective mode, the clearance depends on the mode of dilution (pre- or post-dilution), the blood flow rate and the infusate flow rate. With conventional haemo-filtration, the clearance of small-sized molecules is poorer than that obtained in haemodialysis mode. The clearance in haemo-filtration mode could reach that of haemodialysis if the infusate flow rate, the blood flow and the membrane area were increased. However, this is impractical, increases treatment cost and results in loss of amino acids and hormones. In addition, the blood flow rate is limited, in particular in patients with poor blood access.

Concerning the clearance of small-sized molecules, when it was discovered that this clearance was limited in haemo-filtration mode, the two processes of haemo-filtration and haemodialysis were combined. This simultaneous method was known as haemo-diafiltration. However, problems that arise include difficulty in precisely controlling the haemo-filtration flow, high loss of hormones and amino acids, the complexity of the system, the large quantities of sterile liquid and dialysate necessary, and consequently the high cost of the treatment.

Thus the use of a single filter working in different operating modes still failed to solve the particular problems of loss of molecules in a certain size range, and of high treatment cost.

Figure 1:
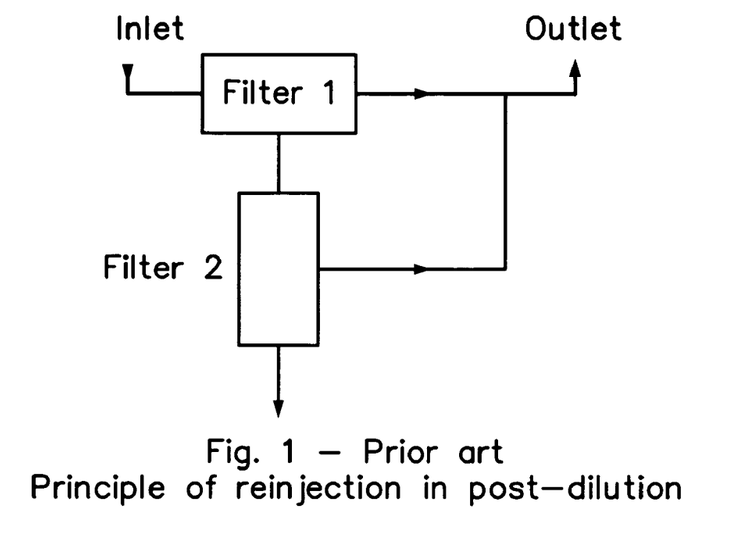
FIG. 1 shows the state of the art concerning the use of two filters with different cut-off values and with post-dilution re-injection.

A proposal was then made by Drs J. C. Kingswood and F. D. Thompson of a continuous haemo-filtration with no re-injection liquid: the treatment of the ultra-filtrate was performed by a second membrane also working in spontaneous ultrafiltration. FIG. 1 represents the dialysis set-up derived from this proposal.

The procedure is to treat a first ultra-filtrate, obtained from a first hollow fibre membrane, by sending it through a second hollow fibre membrane in ultrafiltration mode. A first ultrafiltration is performed through a first high-flow membrane impermeable to molecules larger than 10 000 daltons. The apertures in the second membrane are smaller than those in the first.

As shown in FIG. 1, at the outlet from the first membrane the unfiltered liquid, mainly containing large-sized molecules, is sent to the patient for re-injection. The first ultra-filtrate containing small- and medium-sized molecules is filtered through the second membrane. The liquid not filtered by the second membrane, mainly containing medium-sized molecules, is collected in a waste bag. The second ultra-filtrate, mainly containing small-sized molecules, is re-injected in post-dilution via the patient's venous line.

This saves consuming excessive amounts of sterile liquid in post-injection, and allows re-injection in the patient of a liquid containing few medium-sized molecules.

Even so, a high loss of nutrients, amino acids, glucose and vitamins occurs, and the clearance of small ions such as potassium is poor.

Accordingly, another dialysis device was designed. It was considered that the uraemic molecules that had to be removed were of molecular weight less than 200 daltons or between 10 000 and 40 000 daltons.

Figure 2:
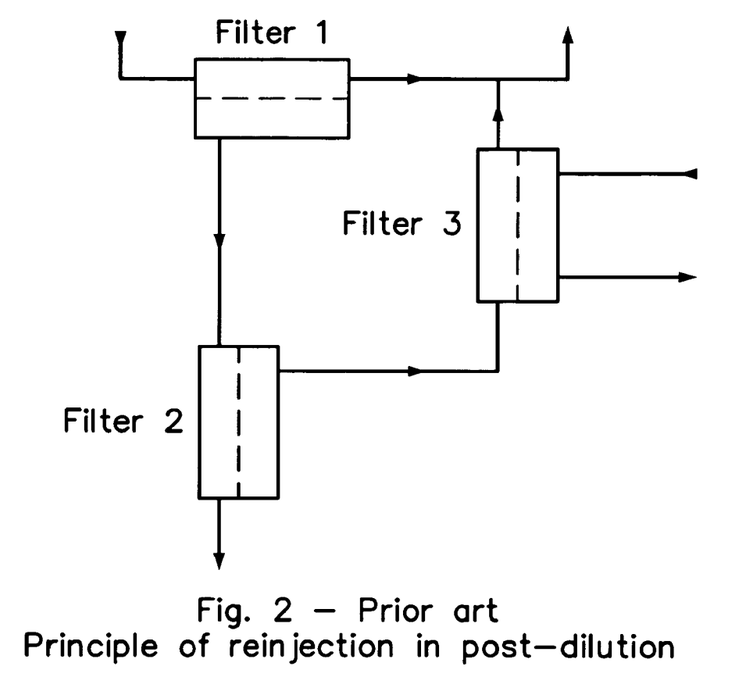
FIG. 2 shows the state of the art concerning the use of three filters with different cut-off values and with post-dilution re-injection.

This consideration gave rise to a device composed of three filters, depicted in FIG. 2.

A first filter has a cut-off value of about 40 000 daltons. The blood flows through this first filter to yield a first filtrate containing small-sized and medium-sized molecules, i.e., molecules of molecular weight less than 40 000 daltons. The solutes of mass between 10 000 and 40 000 daltons are then eliminated by ultrafiltration through the second filter, which has a cut-off value below 10 000 daltons. The second filtrate is then treated by haemo-filtration with a membrane with a cut-off value of about 200 daltons. Thus the purified filtrate, containing solutes between 200 and 10 000 daltons, is returned for post-infusion to the patient, who also receives the molecules of molecular weight greater than 40 000 daltons.

However, the clearance of all the solutes depends on the ultrafiltration rate in filter 1, which cannot exceed 30% of the blood flow, a value that is low compared with that attained in conventional haemodialysis. This raises operating costs.

Figure 3:
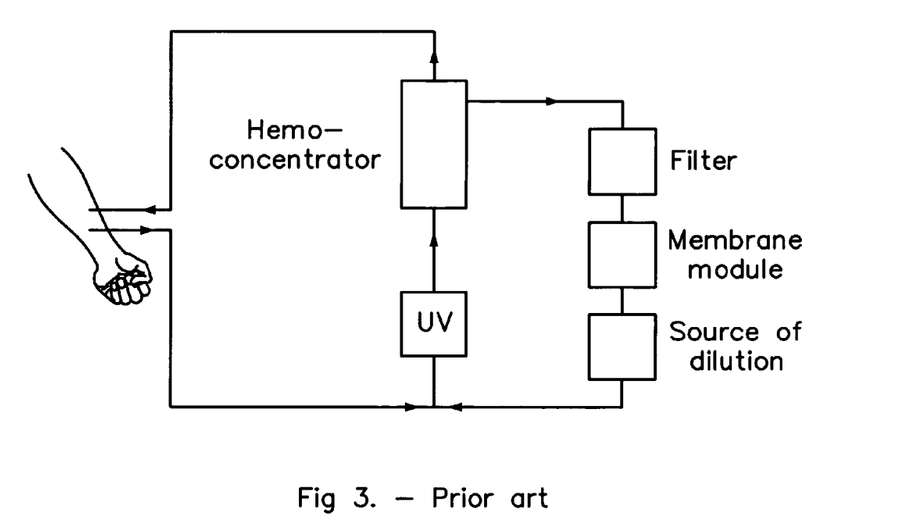
FIG. 3 shows the state of the art of U.S. Pat. No. 6,193,681.

Lastly, U.S. Pat. No. 6,193,681 describes an apparatus to treat septicaemia in the blood, depicted here in FIG. 3. The blood flows first through a UV irradiation device and then through a blood concentrator before re-injection in the patient. A secondary circuit is connected to a second outlet from the blood concentrator from which the fluid flows out through a filter followed by a membrane module and a dilution source, and is then injected upstream of the blood concentrator.

There is in addition an analogous problem with plasmapheresis. Therapeutic exchange plasmapheresis is carried out on patients whose plasma contains one or more harmful or toxic substances.

These solutes are eliminated from the plasma by the same principle as the elimination of solutes from blood, one difference being the greater molecular weight of the solutes to be extracted from the plasma.

Thus recurrent problems have been encountered in the design of the devices in prior art, namely:

High consumption of perfusion liquid,
High losses of nutrients, amino acids, glucose and vitamins,
Poor clearance of solutes,
High cost of devices comprising several filters and pumps.

The problem addressed in this patent application is how to achieve selective elimination of molecules in one or more molecular weight ranges with good clearance, yet consume very small amounts of sterile liquid.

For example, for patients in a state of septicaemia, many medium-sized molecules have to be eliminated, while still maintaining satisfactory elimination of small-sized molecules. Septicaemia is characterised by abundant repeated release of specific pathogenic germs from an initial point of infection.

Another potential problem is optimally adapting such a system for long-term therapy carried out in an intensive care environment without a risk of filter clogging. Such an adaptation can be achieved by judicious choice of mode of operation of the various filters, of use and appropriate positioning of means to regulate flow rate, of controlled flow rates and of hydraulic design of the lines.

SUMMARY OF THE INVENTION

In order to solve the problem outlined above, the invention consists of an extracorporeal blood treatment device comprising at least one exchanger 1 equipped with at least one first inlet 2 for the blood to be treated, a first fluid outlet 4 and a second fluid outlet 5, an input line 10 for blood to be treated connected to the first inlet 2 of the exchanger 1, a blood output line (or venous line) 11 connected to the first outlet 4 of the exchanger 1, at least one treatment unit 21 comprising at least one first fluid inlet 22 and at least one first fluid outlet 24, the second outlet 5 of the exchanger 1 being in fluid communication with the first inlet 22 of the treatment unit 21, where the first outlet 24 from the treatment unit 21 is in fluid communication with the input line 10.

The invention also concerns an extracorporeal blood treatment method to be implemented by means of the extracorporeal blood treatment device comprising an exchanger 1 to which are connected a blood input line 10 and a blood output line 11 and a treatment unit 21, which method comprises the following steps: blood is sent through input line 10 connected to exchanger 1, filtered first in the exchanger 1 to produce a first filtrate, which is filtered at least a second time by the treatment unit 21 to produce a second filtrate, which is sent through the input line 10 for pre-dilution of blood to be treated, and the blood is sent from the outlet from exchanger 1 to the output line 11.

Other advantages and characteristics of the invention will be inferred from the following description.

BRIEF DESCRIPTION OF THE DRAWINGS

The description refers to the appended drawings, where.

DETAILED DESCRIPTION

Figure 4:
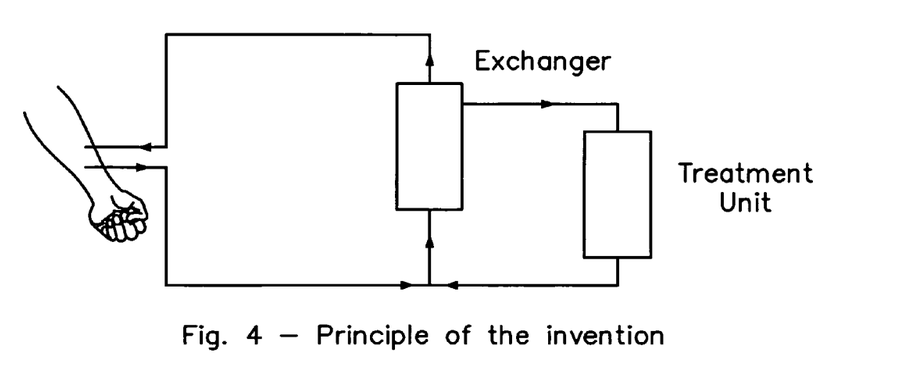
FIGS. 4 to 10 are schematic diagrams of the device for the treatment of physiological fluid according to the invention, together with various embodiments.

FIG. 4 shows the principle of the invention in diagrammatic form: blood inflow through an input line, its arrival in the exchanger and its outflow from the exchanger through an output line, together with the treatment of the first filtrate by a treatment unit and the injection of the liquid leaving the treatment unit in pre-dilution in the arterial line. We can define this concept as a "cascade" of filtration steps with re-injection of the final filtrate in pre-dilution; in detail: a first filtrate is a second time filtrated, and the second filtrate is then injected at the inlet of the first filter, or in "pre-dilution".

Figure 5:
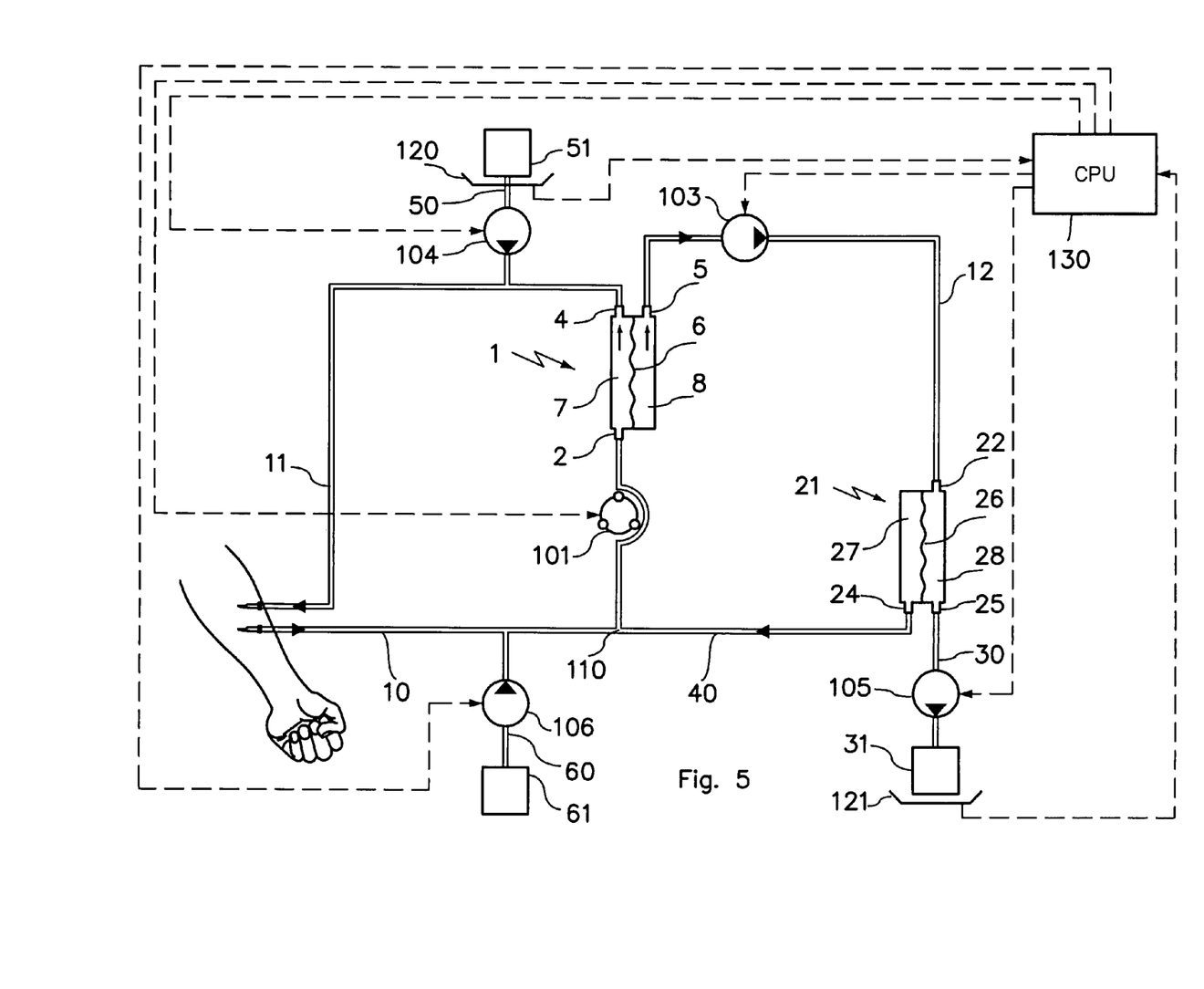

FIG. 5 shows the extracorporeal blood treatment device of the invention consisting of an exchanger 1 comprising a first inlet 2 for the blood to be treated, a first fluid outlet 4 and a second fluid outlet 5, an input line 10 for the blood to be treated, or arterial line, connected to the first inlet 2 of the exchanger 1, a blood output line, or venous line, 11 connected to the first outlet 4 of the exchanger 1. A treatment unit 21 comprises a first fluid inlet 22, and a first fluid outlet 24; the second fluid outlet 25 of the exchanger 1 is in fluid communication with the first inlet 22 of the treatment unit 21, and the first outlet 24 of the treatment unit 21 is in fluid communication with the input line 10.

The fluid communication between the first inlet 22 of the treatment unit 21 and the second outlet 5 of the exchanger 1 is made by a first duct 12.

The exchanger 1 can be equipped with a semi-permeable membrane 6 that divides it into a first chamber 7 and a second chamber 8. The first inlet 2 of the exchanger is in fluid communication with the first chamber 7 of the exchanger, the first outlet 4 of the exchanger is in fluid communication with the first chamber 7 of the exchanger, and the second outlet 5 of the exchanger is in fluid communication with the second chamber 8 of the exchanger.

The blood input line 10, termed the 'arterial line', connected to the first inlet 2 of the exchanger 1, the blood output line 11 termed the 'venous line', connected to the first outlet 4 of the exchanger and the first chamber 7 of the exchanger form part of an extracorporeal blood treatment circuit.

Figure 6:
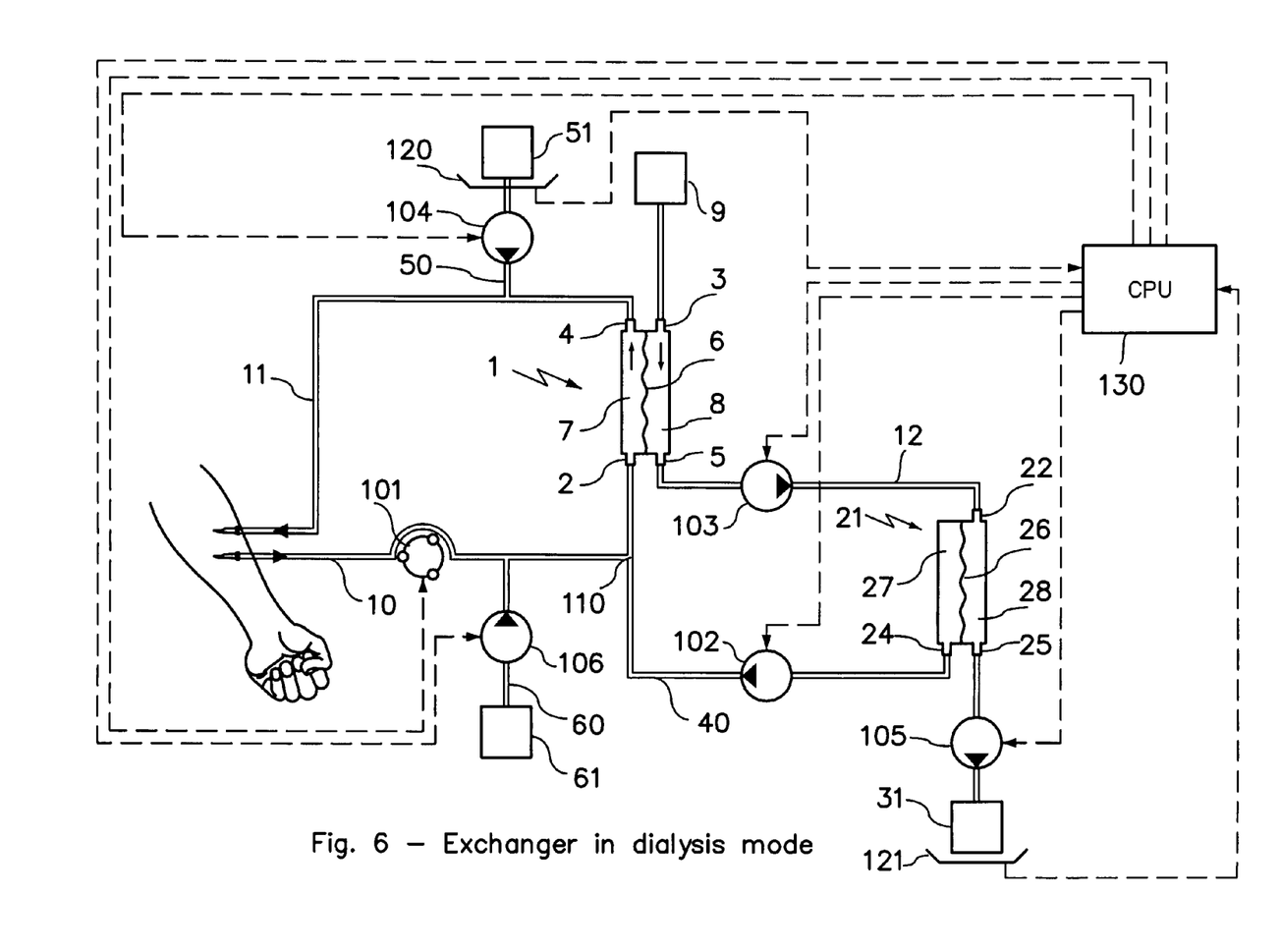

In one embodiment shown in FIG. 6 the exchanger 1 can include a second inlet 3 in fluid communication with the second chamber 8 and in fluid communication with a first source of dialysis liquid 9. In this mode of operation the blood and the dialysis liquid flow in opposite directions in each of the two chambers.

FIG. 5 shows the treatment unit 21 equipped with a semi-permeable membrane 26 that divides it into a first chamber 27 and a second chamber 28.

The treatment unit 21 can advantageously have a second fluid outlet 25.

Thus the first outlet 24 of the treatment unit 21 is in fluid communication with the first chamber 27 of the treatment unit 21 and the second outlet 25 of the treatment unit 21 is in fluid communication with the second chamber 28 of the treatment unit 21.

A first duct 12 is connected between the second outlet 5 of the exchanger 1 and the first inlet 22 of the treatment unit 21, providing the fluid communication.

A second duct 40 is connected between the first outlet 24 of the treatment unit 21 and the first inlet 2 of the exchanger 1, providing the fluid communication.

Alternatively, the first inlet 22 of the treatment unit 21 can be in fluid communication with either the second chamber 28 of the treatment unit 21, or with the first chamber 27 of the treatment unit 21.

The second outlet 25 of the treatment unit 21 is in fluid communication with a first waste liquid discharge line 30, which discharge line 30 can connect the second outlet 25 of the treatment unit 21 to a drain or to a first waste liquid container 31.

Figure 7:
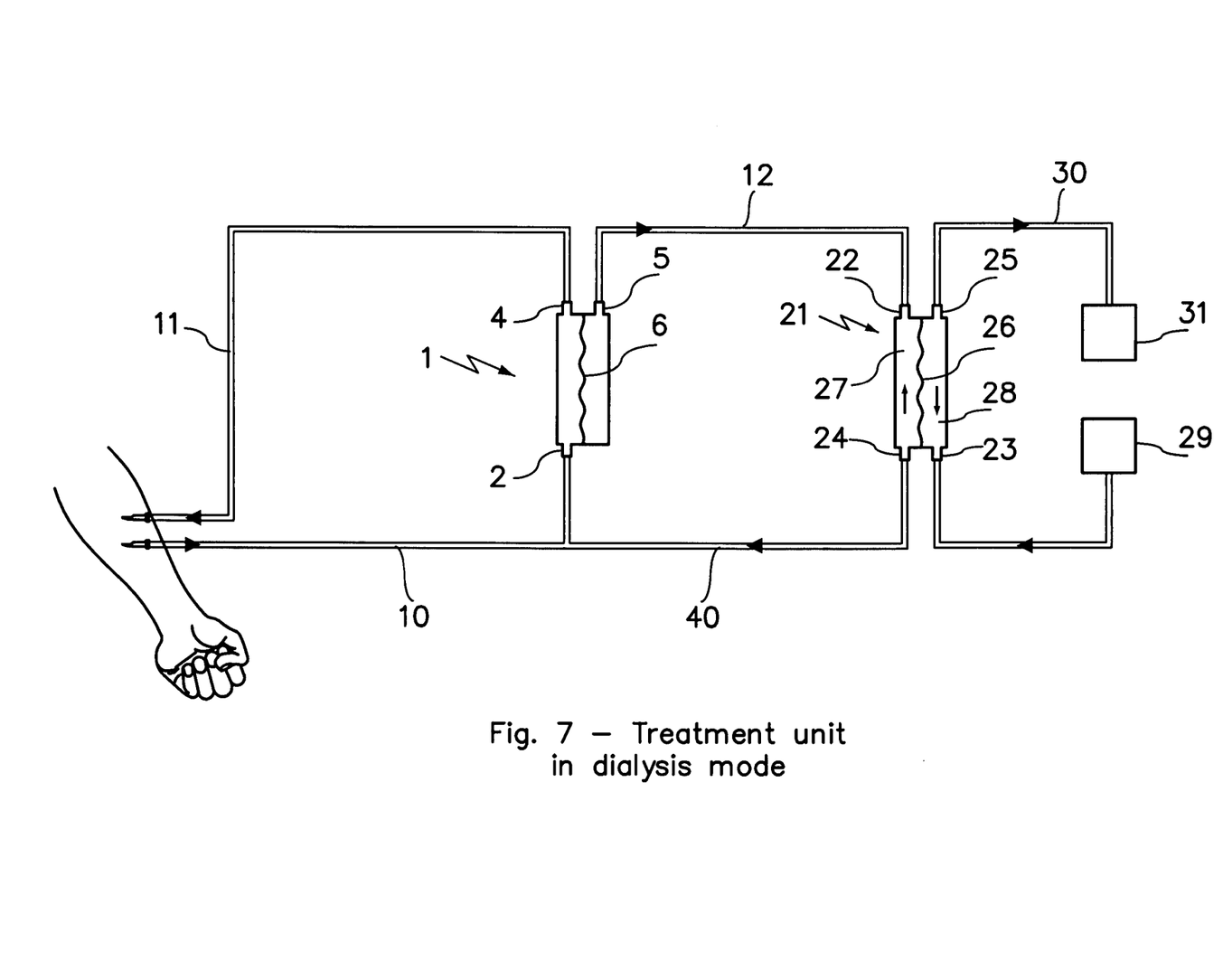

The treatment unit 21 can also have a second inlet 23, which second inlet 23 is in fluid communication with the second chamber 28 and with a second source of dialysis liquid 29. In this operating mode of the treatment unit, shown in FIG. 7, the dialysis liquid flows in the opposite direction to the physiological liquid arriving via the first inlet 22.

The exchanger 1 and the treatment unit 21 have different characteristics. The membrane 6 of the exchanger 1 can be a high flow membrane, and the membrane 26 of the treatment unit 21 can be a low flow membrane.

A low-flow membrane has a low water permeability. The ultrafiltration coefficient is between 2 and 10 ml/h,mmHg, m². A high-flow membrane has a much higher hydraulic permeability. The ultrafiltration coefficient is 20 to 50 mL/h, mmHg,m².

The exchanger or the treatment unit may comprise a hollow fiber dialyser (called also capillary filter) or a plate dialyser, this means with membrane sheets.

Thus the permeability to molecules of the membrane 6 in the exchanger 1 is greater than the permeability to molecules of the membrane 26 in the treatment unit 21, at least above a certain molecular weight.

More particularly, we can define a ratio or a difference between the two cut off values of the first membrane and the second membrane. Thus, we can define ratio of the cut-off value of the first membrane to the cut off value of the second membrane less than or equal to three. In an other way, we can define the difference in cut-off value between the first membrane and the second membrane is between 20 000 and 30 000 daltons. The cut-off value of the first membrane might be less than or equal to 40 000 daltons, and the cut-off value of the second membrane might be less than or equal to 10 000 daltons. In one embodiment the cut-off value of the first membrane is approximately 40 000 daltons and the cut-off value of the second membrane is approximately 10 000 daltons.

To re-infuse water to the patient being treated, it is possible to connect to the output line 11 a post-dilution line 50 connected to a first source of sterile liquid 51 and (or) to the input line 10 a pre-dilution line 60 connected to a second source of sterile liquid 61.

A second duct 40 makes a fluid connection between the first outlet 24 of the treatment unit 21 and the first inlet 2 of the exchanger 1.

The pre-dilution line 60 can be connected directly to said second duct 40 or directly to input line 10.

The different sources of sterile liquid 51, 61 can be bags of sterile liquid and (or) can be obtained by on-line preparation of sterile liquid from water drawn from a main supply system.

Figure 9:
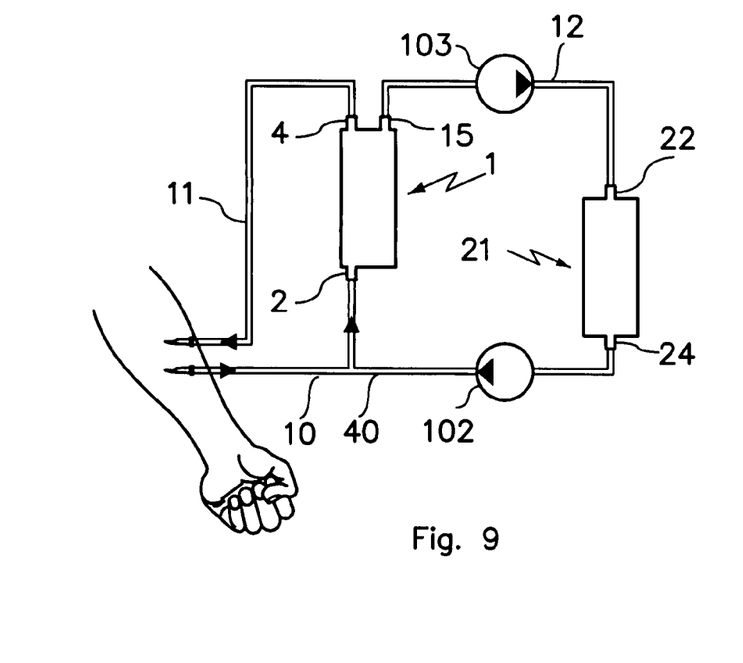
Figure 10:
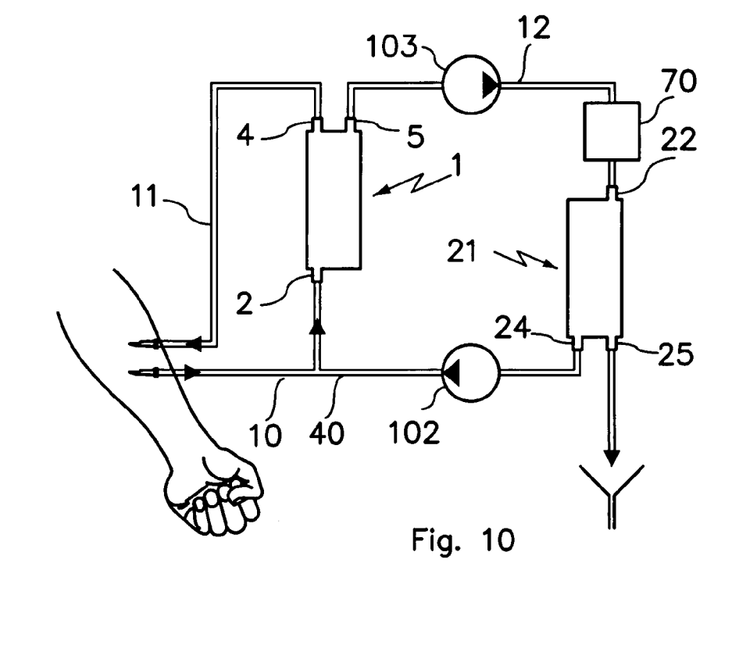

In the application of this invention to the special case of plasmapheresis, shown in FIGS. 9 and 10, the exchanger is a plasma filter. The plasma filter has a cut-off value between one million and five million daltons.

In this application, the exchanger or the treatment unit may comprise a hollow fiber dialyser (also called capillary filter) or a plate dialyser, this means with membrane sheets.

Thus the treatment unit 21 includes a unit able to fixate at least one given substance. This unit can be an adsorption cartridge, or a reactor, for example an electropheresis cell.

The treatment unit can be equipped with a semi-permeable membrane 26 that divides it into a first chamber 27 with a first outlet 24 and a second chamber 28 with a first inlet 22 and a second outlet 25. The second outlet is connected to a discharge line. The treatment unit can have a cut-off value less than or equal 250 000 daltons.

The cut off value can be less than or equal to 200000 dalton.

The treatment unit can have a cut-off value such that almost 100% of the albumin molecules (with 58000 daltons as molecular weigh) can pass through the membrane.

FIG. 10 shows a device comprising means to act on at least certain molecules 70. These means are connected to the first tube 12 between the second outlet 5 of the exchanger 1 and the first inlet 22 of the treatment unit 21. These means to act on at least certain molecules 70 can be a reactor, an adsorber or a radiation-based device, for example an electropheresis, enzyme reaction, radiation, or ultraviolet irradiation device. The plasma filter can then have pores of one micron. The treatment unit can have a cut-off value less than or equal to 90 000 daltons, letting proteins through to the patient's blood.

Figure 8:
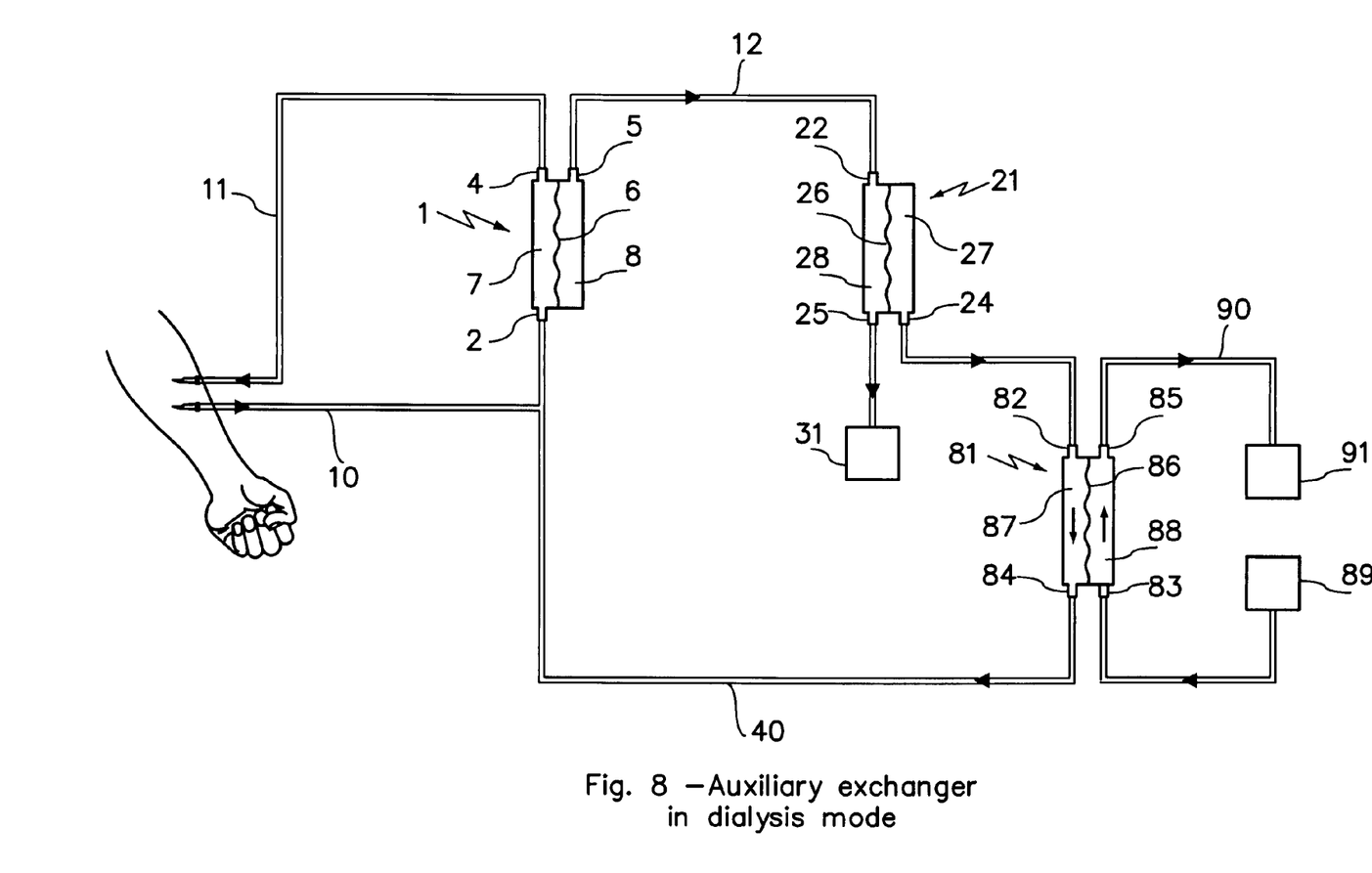

Another feature of the invention is that it adds a third means of filtration to eliminate a further molecular weight range, shown in FIG. 8. The device can comprise at least one auxiliary exchanger 81 with a membrane 86 that separates it in a first chamber 87 that is in fluid communication with a first inlet 82 and a first outlet 84 and in a second chamber 88 in fluid communication with at least one second outlet 85. The cut-off value of such an auxiliary exchanger will be less than the cut-off values of the other two membranes (6, 26).

The first inlet 82 of the auxiliary exchanger 81 is in fluid communication with the second outlet 24 of the treatment unit 21, and one of the two outlets 84 or 85 of the auxiliary exchanger 81 is in fluid communication with the first inlet 2 of the exchanger 1.

A second waste liquid discharge line 90 connects the other outlet 84 or 85 of the auxiliary exchanger 81 to a drain, which drain can be a second waste liquid container 91.

FIG. 8 shows the auxiliary exchanger operating in dialysis mode: the auxiliary exchanger 81 has a second inlet 83 in fluid communication with the second chamber 88 of the auxiliary exchanger 81 and in fluid communication with a third source of dialysis liquid 89, the first outlet 84 of the auxiliary exchanger 81 being in fluid communication with the first inlet 82 of the exchanger 1, the second outlet 85 of the auxiliary exchanger 81 being in fluid communication with a drain 91 via a second waste liquid discharge line 90.

The choice of the three membranes will be made very precisely according to the patient and the treatment required according to the molecular weight ranges that are to be eliminated or retained. The first membrane 6 is appropriate for molecules of high molecular weight (preferentially in haemo-filtration mode), the second membrane 26 is appropriate for molecules of mid-range molecular weight (preferentially in haemo-filtration mode), and the third membrane 86 is appropriate for molecules of low molecular weight, i.e., preferentially in dialysis mode. The auxiliary exchanger 81 can still operate in ultrafiltration mode if necessary. The choice of operating mode allows the treatment to be tailored to patient needs and to obtain optimal running with minimal clogging.

Concerning the regulation of the various fluid flow rates, first means for regulating active liquid flow rate 101 is placed on the input line 10 connected to the first inlet 2 of the exchanger 1. Alternatively, the first means to regulate flow rate (101) can be placed exactly between the first inlet 2 of the exchanger 1 and the connection point 110 connecting the input line to the duct or upstream of the connecting point 110 connecting the input line 10 to the second duct 40.

In the first alternative, the pressure drop in the second duct 40 requires a lower positive pressure in the first duct 12 to reach the desired trans-membrane pressure (TMP) of the membrane 26.

Also, in the first alternative, it is not necessary to fit a pump on the second duct 40: a single pump 101 suffices for the second duct 40 and the arterial line 11.

In the second alternative, second means for regulating active liquid flow rate 102 is placed on the second duct 40 connecting the first outlet 24 of the treatment unit 21 to the first inlet 2 of the exchanger 1.

Third means for regulating active liquid flow rate 103 is placed on the first duct 12 connecting the second outlet 5 of the exchanger 1 to one of the inlets 22 or 23 of the treatment unit 21.

Also, fourth means for regulating active liquid flow rate 104 can be connected to the post-dilution line 50.

Fifth means for regulating active liquid flow rate 105 can be connected to the waste liquid discharge line 30 connecting the second outlet 25 of the treatment unit 21 to a drain 31.

In the configuration with at least three means of regulating flow rate 101 on the input line, 102 on the second duct 40 and 105 on the discharge line 30, special care must be taken to make sure the different flow rates set are compatible.

Sixth means for regulating active liquid flow rate 106 can be connected to the pre-dilution line 60.

The means for regulating flow rate 101, 102, 103, 104 and 105 can be pumps and (or) valves. In particular, the means for regulating flow rate on the discharge line 30, or on the post-dilution line 50 or the pre-dilution line 60 will be valves.

In a specific embodiment, the first post-dilution sterile liquid source 51 is a bag of sterile liquid and the first waste liquid container 31 connected to the discharge line leaving the treatment unit is a bag of waste liquid. The device comprises a first balance 120 to weigh the bag of sterile liquid 51 and a second balance 121 to weigh the bag of waste liquid 31. Alternatively, a single balance 120-121 can weigh the bag of sterile liquid 51 together with the bag of waste liquid 31.

In this case, a calculation and control unit 130 will receive the signals emitted by at least one balance 120-121 and will control the means for regulating liquid flow rate 101, 102, 103, 104 and 105.

In an embodiment, the device comprises a post-dilution line (50) connected, at one end, to the output line 11, and, at its other end, to a first source of sterile liquid (51); the device also includes fourth means for regulating liquid flow rate (104) placed on the post-dilution line (50), a balance (120, 121) to weigh the bag of sterile liquid (51) and the bag of waste liquid (31), fifth means for regulating liquid flow rate (105) placed on the waste liquid discharge line (30) connecting the second outlet (25) of the treatment unit (21) to a drain (31). The calculation and control unit (130) receives signals emitted by the balance (120, 121) and controls either the fourth means, or fifth means (105) or both the fourth and the fifth means to independently regulate the flow rate in each respective conduit.

According to an alternative solution, the device comprises a first independent balance (120) to weigh the bag of sterile liquid (51) and a second independent balance (121) to weigh the bag of waste liquid (31). The calculation and control unit (130) receives signals emitted by first and second balances (120, 121) and independently controls the fourth means to regulate liquid flow rate (104), and the fifth means to regulate liquid flow rate (105).

The calculation and control unit will periodically calculate the real flow rate or a parameter that is a function of the real flow rate, for example from the weight and the time interval between each two measurements. It will compare the real flow rate measured to the desired flow rate and will be able to control one or more means for regulating active liquid flow rate (101, 102, 103, 104, or 105).

Thus the quantities of sterile liquid and waste liquid, or their difference, can be monitored and controlled during the treatment. Knowing these weight quantities, the control unit can obtain a desired quantity of sterile liquid solution and waste liquid.

The hydric equilibrium can be well controlled in this way.

The device described above is applicable to plasmapheresis.

The invention also concerns a method for the extracorporeal treatment of blood to be implemented on a device for the extracorporeal treatment of blood comprising an exchanger 1 to which are connected a blood input line 10 and a blood output line 11, and a treatment unit 21, which method comprises the following steps:

blood is sent through the input line 10 connected to the first inlet of the exchanger 1, The blood is first filtered in the exchanger 1, producing a first filtrate passing through the second outlet of the exchanger, the first filtrate is filtered at least a second time in the treatment unit 21, producing a second filtrate, the second filtrate is sent through the first outlet of the treatment unit to the input line 10 to effect a pre-dilution of the blood to be treated, the blood is sent out from the first outlet of the exchanger to the output line 11.

In particular, the method will include a second filtration carried out through a semi-permeable membrane 26 in a treatment unit 21 divided into a first chamber 27 and a second chamber 28, yielding the second filtrate and sending the non-filtered liquid to the drain line 30.

Another feature of the method is that the first filtration is carried out through a semi-permeable membrane 6 that divides the exchanger 1 into a first chamber 7 and a second chamber 8.

Another feature of the method is that the membrane 26 of the treatment unit filters molecules of molecular weight less than the molecular weight of the molecules filtered from the membrane 16 of the exchanger.

Another feature of the invention is that the method includes a step in which a sterile liquid is perfused in the blood output line 11 of the exchanger.

Another feature of the invention is that the method includes a step in which a sterile liquid is perfused in the blood input line 10 of the exchanger.

Another feature of the invention is that the method uses an exchanger membrane 16 with a cut-off value less than 40 000 dalton.

Another feature of the invention is that the method uses an exchanger membrane 16 with a cut-off value less than 10 000 dalton.

Another feature of the invention is that the treatment carried out is a plasmapheresis and the treatment unit fixates at least one certain given substance.

Another feature of the invention is that the exchanger membrane 16 has a cut-off value between one million and five million dalton.

Another feature of the invention is that the treatment unit membrane 16 has a cut-off value less than 250 000 dalton.

Figure 11:
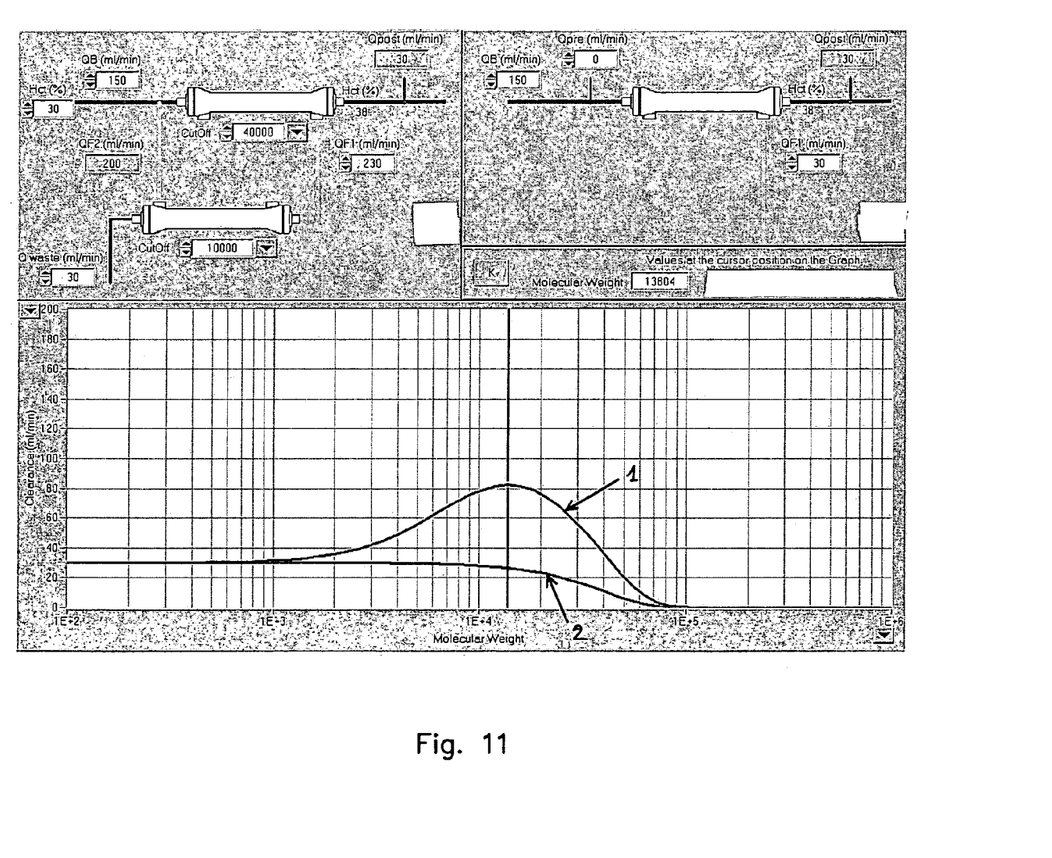
FIGS. 11 and 12 show the estimated results in terms of clearance according to the molecular size of the solutes for two configurations of the device according to the invention.
Figure 12:
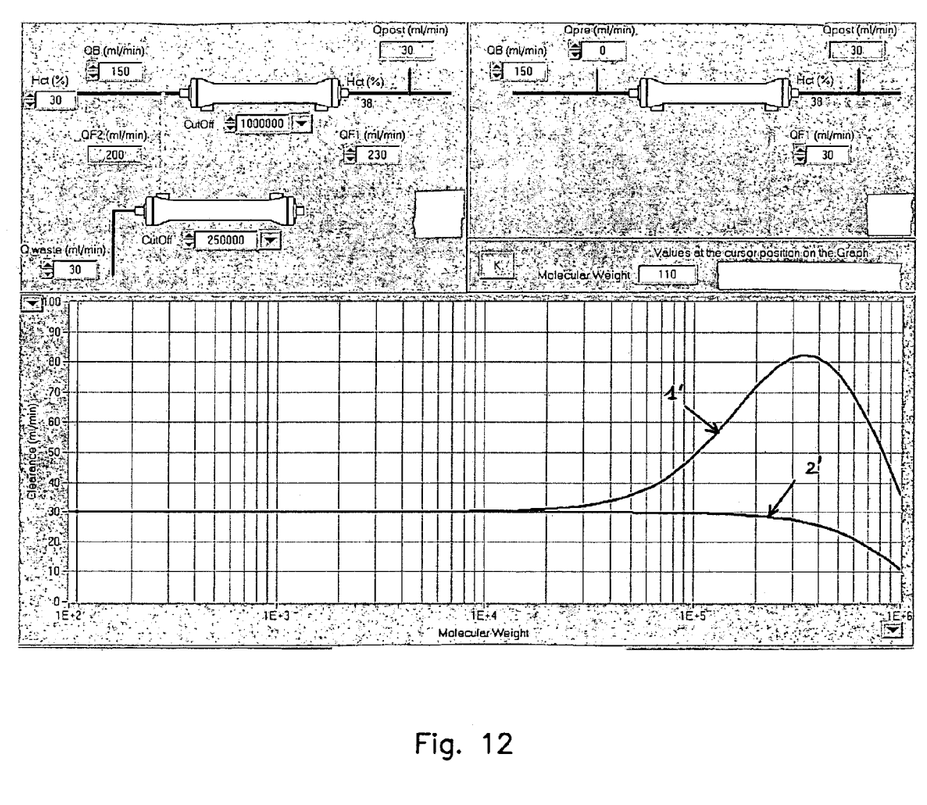

Simulations have been performed using filters with different cut-off values. FIGS. 11 and 12 show the estimated results in terms of clearance as a function of the molecular weight of solutes for two configurations of the device according to the invention. FIG. 11 shows a first configuration using an exchanger with a cut-off value equal to 40 000 daltons, and a treatment unit using an exchanger with a cut-off value equal to 10 000 daltons. The clearance (curve 1) for molecules of molecular weight about 11 000 daltons is very good, while the clearance of small molecules is kept constant relative to an operating device equipped with a single filter (curve 2).

FIG. 12 shows a second configuration for plasmapheresis using an exchanger with a cut-off value equal to 1 000 000 dalton, and a treatment unit using an exchanger with a cut-off value equal to 250 000 dalton. The clearance (curve 1') for molecules of molecular weight about 300 000 dalton is very good, while the clearance of medium-sized molecules is kept constant relative to an operating device equipped with a single filter (curve 2').

The invention offers numerous advantages. It allows:

A three- to fourfold increase in the clearance of medium-sized molecules (or large-sized molecules in plasmapheresis) relative to a standard long-term treatment, with no increase in the quantity of exchange liquid and with no change in the standard clearance of small-sized molecules (small- and medium-sized in plasmapheresis), Large savings in sterile liquid, and therefore lower operating costs, Sufficient elimination of medium-sized molecules, Retention of trace elements and nutrients, which are returned to the patient, High volume filtration.

In particular, in the configuration illustrated in FIG. 5, many other advantages are offered. Minimal means of regulating flow rate are required: a peristaltic pump 101 on the arterial line and a pump 103 on the second duct 40 are sufficient to operate the device.

Also, the positioning of the means for regulating flow rate is well conceived: there is not necessarily any need for a pump on the second duct 40, although one can still be fitted, and the means of regulating flow rate 103 need not be very powerful. This permits long-term operation for intensive care while avoiding heavy pore clogging of the various membranes.

Lastly, application of this operating scheme is envisaged for another mode of extracorporeal blood treatment, namely plasmapheresis. Plasmapheresis operation is optimal when the membranes are carefully chosen and used.

The invention claimed is:

1. A device for the extracorporeal treatment of blood comprising:

at least one exchanger comprising a semi-permeable membrane dividing said exchanger into a first chamber and a second chamber, at least one first inlet for blood to be treated being in fluid communication with the first chamber of the exchanger, a first fluid outlet being in fluid communication with the first chamber of the exchanger and a second fluid outlet being in fluid communication with the second chamber of the exchanger;

an input line for blood to be treated connected to the first inlet of the exchanger;

a blood output line connected to the first outlet of the exchanger;

at least one treatment unit comprising a semi-permeable membrane dividing the treatment unit into a first chamber and a second chamber, the treatment unit having at least one first fluid inlet in fluid communication with the second chamber of the treatment unit and at least one first fluid outlet in fluid communication with the first chamber of the treatment unit;

the second outlet of the exchanger being in fluid communication with the first inlet of the treatment unit; and the first outlet of the treatment unit being in fluid communication with the input line;

wherein:

the treatment unit includes a second fluid outlet in fluid communication with the second chamber of the treatment unit; and the second outlet of the treatment unit is in fluid communication with a first waste liquid discharge line, the first waste liquid discharge line having a first end and a second end, the first end of said first waste liquid discharge line being connected with the second outlet of the treatment unit and the second end of said first waste liquid discharge line not being connected with any other outlet or inlet of the same treatment unit.

2. A device according to claim 1, wherein a first duct is connected between the second outlet of the exchanger and the first inlet of the treatment unit.

3. A device according to claim 1, wherein a second duct is connected between the first outlet of the treatment unit and the first inlet of the exchanger.

4. A device according to claim 1, comprising a first waste liquid discharge line connecting the second outlet of the treatment unit to a first waste liquid container.

5. A device according to claim 1, wherein the molecular permeability of the membrane of the exchanger is greater than the molecular permeability of the membrane of the treatment unit, at least above a certain molecular weight.

6. A device according to claim 5, wherein the membrane of the exchanger is a high-flow membrane and the membrane of the treatment unit is a low-flow membrane.

7. A device according to claim 5, wherein a ratio of a cut-off value of the membrane of the exchanger to a cut-off value of the membrane of the treatment unit is less than or equal to 3.

8. A device according to claim 5, wherein a difference in a cut-off value between the membrane of the exchanger and the membrane of the treatment unit lies between 20 000 dalton and 30 000 dalton.

9. A device according to claim 5, wherein a cut-off value of the membrane of the exchanger is less than or equal to 40 000 dalton.

10. A device according to claim 5, wherein a cut-off value of the membrane of the treatment unit is less than or equal to 10 000 dalton.

11. A device according to claim 1, further comprising a post-dilution line having a first end connected to the output line and a second end connected to a first source of sterile liquid.

12. A device according to claim 1 or 11, further comprising a pre-dilution line having a first end connected to the input line and a second end connected to a second source of sterile liquid.

13. A device according to claim 12, wherein the pre-dilution line is connected directly to a duct connected between the first outlet of the treatment unit and the first inlet of the exchanger.

14. A device according to claim 12, wherein the pre-dilution line is connected directly to the input line.

15. A device according to claim 12 wherein, at least one source of sterile liquid is a bag of sterile liquid.

16. A device according to claim 1, wherein the exchanger is a plasma filter.

17. A device according to claim 16, wherein the plasma filter has a cut-off value between one million and five million dalton.

18. A device according to claim 16 or 17, wherein the treatment unit has a cut-off value less than or equal to 250 000 dalton.

19. A device according to claim 18 wherein, the treatment unit comprises a semi-permeable membrane having a cut-off value such that all albumin molecules pass through said membrane.

20. A device according to claim 2, further comprising a reactor active on the first duct.

21. A device according to claim 2, further comprising an adsorption device active on the first duct.

22. A device according to claim 2, further comprising a radiation device active on the first duct.

23. A device according to claim 1, further comprising first means for regulating liquid flow rate placed on the input line connected to the first inlet of the exchanger.

24. A device according to claim 1, further comprising a first duct connecting the second outlet of the exchanger and the first inlet of the treatment unit; and
first means for regulating liquid flow rate placed on the input line exactly between the first inlet of the exchanger and a connection point connecting the input line to the second duct.

25. A device according to claim 1, further comprising a first duct connecting the second outlet of the exchanger and the first inlet of the treatment unit;
a second duct connecting the first outlet of the treatment unit and the first inlet of the exchanger;
means for regulating liquid flow rate placed on the input line upstream of the connection point connecting the input line to the second duct; and
means for regulating liquid flow rate placed on the second duct.

26. A device according to claim 1, further comprising a first duct connecting the second outlet of the exchanger and the first inlet of the treatment unit; and
means for regulating liquid flow rate placed on the first duct connecting the second outlet of the exchanger to the first inlet of the treatment unit.

27. A device according to claim 1, further comprising a post-dilution line having a first end connected to the output line and a second end connected to a first source of sterile liquid; and
means for regulating liquid flow rate placed on the post-dilution line.

28. A device according to claim 1, further comprising means for regulating a liquid flow rate placed on the waste liquid discharge line and connecting the second outlet of the treatment unit to a drain.

29. A device according to claim 12, further comprising means for regulating liquid flow rate placed on the pre-dilution line.

30. A device according to claim 1, further comprising a bag containing a first source of sterile liquid for post-dilution, and a first waste liquid container connected to the discharge line from the treatment unit being a bag for receiving waste liquid.

31. A device according to claim 30, further comprising a balance to weigh the bag of sterile liquid and the bag of waste liquid.

32. A device according to claim 31 wherein, said balance comprises a first independent balance to weigh the bag of sterile liquid and a second independent balance to weigh the bag of waste liquid.

33. A device according to claim 30, further comprising:
a post-dilution line connected, at one end, to the output line, and, at its other end, to a first source of sterile liquid;
means for regulating liquid flow rate placed on the post-dilution line;
a balance to weigh the bag of sterile liquid and the bag of waste liquid;
means for regulating liquid flow rate placed on the waste liquid discharge line connecting the second outlet of the treatment unit to a drain; and
a calculation and control unit to receive weight signals emitted by the balance and to control one or both of the means for regulating liquid flow rate placed on the post-dilution line and the means for regulating liquid flow rate placed on the waste liquid discharge line.

34. A device according to claim 33, wherein said balance comprises a first independent balance to weigh the bag of sterile liquid and a second independent balance to weigh the bag of waste liquid, said calculation and control unit receiving first and second weight signals emitted by the first and second balances and independently controlling the means for regulating liquid flow rate placed on the post-dilution line and the means for regulating liquid flow rate placed on the waste liquid discharge line as a function of said first and second weight signals.

35. A method for the extracorporeal treatment of blood to be implemented on a device for the extracorporeal treatment of blood comprising:

an exchanger comprising a semi-permeable membrane dividing said exchanger into a first chamber and a second chamber, at least one first inlet for blood to be treated in fluid communication with the first chamber of the exchanger, a first fluid outlet in fluid communication with the first chamber of the exchanger and a second fluid outlet in fluid communication with the second chamber of the exchanger;
   a blood input line for blood to be treated connected to the first inlet of the exchanger;
   a blood output line connected to the first outlet of the exchanger; and
   a treatment unit comprising a semi-permeable membrane dividing said treatment unit into a first chamber to which at least one first fluid outlet is connected, and comprising a second chamber to which at least one first fluid inlet and a second fluid outlet are connected;
   the method comprising the following steps:
   sending blood through the input line connected to the exchanger;
   filtering blood first in the exchanger, producing a first filtrate;
   filtering the first filtrate at least a second time in the treatment unit, producing a second filtrate;
   sending the second filtrate through the input line to effect a pre-dilution of the blood to be treated;
   sending the blood out from the exchanger to the output line; and
   sending a non-filtered liquid from the second chamber of the treatment unit to a waste drain line, without returning any fluid passing through said waste drain line to any other inlet or outlet of said treatment unit, said waste drain line being connected to the second fluid outlet of the treatment unit.

36. A method according to claim 35, wherein the second filtration step filters through the membrane of the treatment unit molecules of molecular weight less than the molecular weight of the molecules filtered by the membrane of the exchanger during the first filtration step.

37. A device for the extracorporeal treatment of blood comprising:

at least one exchanger comprising a semi-permeable membrane dividing said exchanger into a first chamber and a second chamber, at least one first inlet for blood to be treated being in fluid communication with the first chamber of the exchanger, a first fluid outlet being in fluid communication with the first chamber of the exchanger and a second fluid outlet being in fluid communication with the second chamber of the exchanger;
   an input line for blood to be treated connected to the first inlet of the exchanger;
   a blood output line connected to the first outlet of the exchanger;
   at least one treatment unit comprising a semi-permeable membrane dividing the treatment unit into a first chamber and a second chamber, the treatment unit having at least one first fluid inlet in fluid communication with the second chamber of the treatment unit and at least one first fluid outlet in fluid communication with the first chamber of the treatment unit;
   a first tube having only a first end and a second end, the first end of said first tube being connected only with the second outlet of the exchanger, and the second end of said first tube being connected only with the first inlet of the treatment unit; and
   the first outlet of the treatment unit being in fluid communication with the input line;
   wherein:
   the treatment unit includes a second fluid outlet in fluid communication with the second chamber of the treatment unit; and
   the second outlet of the treatment unit is in fluid communication with a first waste liquid discharge line.

38. A method for the extracorporeal treatment of blood to be implemented on a device for the extracorporeal treatment of blood comprising:

an exchanger comprising a semi-permeable membrane dividing said exchanger into a first chamber and a second chamber, at least one first inlet for blood to be treated in fluid communication with the first chamber of the exchanger, a first fluid outlet in fluid communication with the first chamber of the exchanger and a second fluid outlet in fluid communication with the second chamber of the exchanger;
   a blood input line for blood to be treated connected to the first inlet of the exchanger;
   a blood output line connected to the first fluid outlet of the exchanger; and
   a treatment unit comprising a semi-permeable membrane dividing said treatment unit into a first chamber to which at least one first fluid outlet is connected, and comprising a second chamber to which at least one first fluid inlet and a second fluid outlet are connected;
   a first tube having a first end and a second end, the first end of said first tube being connected only to the second fluid outlet of the exchanger, and the second end of said first tube being connected only to the first fluid inlet of the treatment unit;
   the first fluid outlet of the treatment unit being in fluid communication with the blood input line;
   the method comprising the following steps:
   sending blood through the input line connected to the exchanger;
   filtering blood first in the exchanger, producing a first filtrate;
   filtering all of the first filtrate coming from the second fluid outlet of the exchanger and flowing only via said first tube at least a second time by introducing all of said first filtrate in the first fluid inlet of the treatment unit;
   sending the first filtrate, after said first filtrate has been filtered a second time, through the input line to effect a pre-dilution of the blood to be treated;
   sending the blood out from the exchanger to the blood output line; and
   sending a non-filtered liquid from the second chamber of the treatment unit to a waste drain line, said waste drain line being connected to the second fluid outlet of the treatment unit.

* * * * *

UNITED STATES PATENT AND TRADEMARK OFFICE
CERTIFICATE OF CORRECTION

| | | |
|---|---|---|
| PATENT NO. | : 7,291,269 B2 | Page 1 of 1 |
| APPLICATION NO. | : 10/801830 | |
| DATED | : November 6, 2007 | |
| INVENTOR(S) | : Jacques Chevallet et al. | |

It is certified that error appears in the above-identified patent and that said Letters Patent is hereby corrected as shown below:

In claim 28, column 12, line 35, "outlet-of" should read --outlet of--.

Signed and Sealed this

Twenty-ninth Day of April, 2008

JON W. DUDAS
*Director of the United States Patent and Trademark Office*